US005886348A

United States Patent [19]

Lessure et al.

[11] Patent Number: 5,886,348

[45] Date of Patent: Mar. 23, 1999

[54] NON-DISPERSIVE INFRARED GAS ANALYZER WITH INTERFERING GAS CORRECTION

[75] Inventors: Harold S. Lessure; Satoru Simizu; Louis J. Denes; Alberto M. Guzman, all of Pittsburgh, Pa.

[73] Assignee: American Intell-Sensors Corporation, Pittsburgh, Pa.

[21] Appl. No.: 801,942

[22] Filed: Feb. 14, 1997

[51] Int. Cl.[6] .......... G01N 21/35

[52] U.S. Cl. .......... 250/339.13; 250/339.03; 250/339.04; 250/343

[58] Field of Search .......... 250/339.01, 339.02, 250/339.03, 339.04, 339.06, 339.12, 339.13, 343, 345, 338.3; 356/440

[56] References Cited

U.S. PATENT DOCUMENTS

| | | | |
|---|---|---|---|
| 3,904,880 | 9/1975 | Benz et al. | 250/339.13 |
| 4,560,875 | 12/1985 | Crowder | 250/339.13 |
| 4,914,719 | 4/1990 | Conlon et al. | 250/339.13 |
| 5,026,992 | 6/1991 | Wong . | |
| 5,047,639 | 9/1991 | Wong . | |
| 5,053,754 | 10/1991 | Wong . | |
| 5,055,690 | 10/1991 | Bonne | 250/339.13 |
| 5,060,505 | 10/1991 | Tury et al. . | |
| 5,060,508 | 10/1991 | Wong . | |
| 5,079,422 | 1/1992 | Wong . | |
| 5,103,096 | 4/1992 | Wong . | |
| 5,130,544 | 7/1992 | Nilsson | 250/339.03 |
| 5,332,901 | 7/1994 | Eckles et al. | 250/339.01 |
| 5,335,534 | 8/1994 | Wong | 250/343 |
| 5,418,366 | 5/1995 | Rubin et al. | 250/339.13 |
| 5,429,805 | 7/1995 | Uno et al. . | |
| 5,444,249 | 8/1995 | Wong . | |
| 5,453,620 | 9/1995 | Wadsworth et al. . | |
| 5,468,961 | 11/1995 | Gradon et al. . | |
| 5,468,962 | 11/1995 | Ohishi et al. . | |
| 5,542,285 | 8/1996 | Merilainen et al. | 250/343 |
| 5,559,333 | 9/1996 | Araya et al. | 250/343 |
| 5,600,142 | 2/1997 | Van Den Berg et al. | 250/339.13 |

*Primary Examiner*—Constantine Hannaher
*Assistant Examiner*—Darren M. Jiron
*Attorney, Agent, or Firm*—Kirkpatrick & Lockhart LLP

[57] ABSTRACT

An infrared gas analyzer for measuring low concentrations of a target gas, on the order of parts per million, in a sample gas is comprised of a gas sampling chamber, an infrared light source, and a power source for energizing the light source. A plurality of filters is provided to transmit infrared radiation at certain wavelengths. The wavelengths are chosen such that the effects of unwanted gases (such as water and carbon dioxide) can be removed from the final output signal. A plurality of infrared detectors are responsive to the filters for producing a plurality of electrical signals. A circuit is provided for combining the plurality of electrical signals to produce an output signal representative of the concentration of the target gas independently of other gases in the sample gas. A method of measuring low concentrations of a target gas is also disclosed.

53 Claims, 10 Drawing Sheets

5V POWER SUPPLY
10V POWER SUPPLY
1.5Hz LAMP DRIVER
TOP BOARD
BYPASS CAPACITORS
FOR U1,U2,U3,U4
(TO HEATER)
(To Lamp)
12V INPUT
MAX RANGE
ZERO
SPAN
LAMP
CO2
N2O
REF

NON-DISPERSIVE INFRARED GAS ANALYZER WITH INTERFERING GAS CORRECTION

CROSS REFERENCE TO RELATED APPLICATIONS

Not applicable

FEDERALLY SPONSORED RESEARCH

Not applicable

BACKGROUND OF THE INVENTION

Field of the Invention

The present invention relates to non-dispersive infrared gas analyzers, and more particularly, to a non-dispersive infrared gas analyzer with a circuit for compensating for interfering gases that are present in a sample gas, a circuit for stabilizing the temperature of infrared sensors, and/or a circuit for compensating for lamp degradation due to lamp aging effects.

Description of the Background of the Invention

Non-dispersive infrared (NDIR) gas analyzers are used to measure the concentration of a particular target gas component of a sample gas. NDIR analyzers measure the infrared radiation absorbed by the target gas component of the sample gas and thus give a measure of the concentration of each component. NDIR analyzers typically have high measuring sensitivity and high selectivity. However, the sensitivity of NDIR gas analyzers is dependent on the relative humidity of the operating environment, the concentration of interfering gases such as carbon dioxide, the thermal sensitivity of infrared detectors, and the effects of lamp degradation on infrared light sources. Thus, NDIR gas analyzers typically cannot measure the concentration of a target gas in the parts per million range.

FIG. 1 illustrates a conventional NDIR gas analyzer. The sample gas is introduced either actively or passively into a sample gas measuring cell 1. Infrared rays are emitted into the measuring cell 1 from an infrared source 2. An optical filter, such as a bandpass filter 3 having a pass band wavelength equal to that of the target gas component is located at one end of the measuring cell between the infrared source 2 and a detection area 4. The infrared rays are absorbed in the measuring cell 1 according to the concentrations of the target gas components. The unabsorbed rays are transmitted to the bandpass filter 3, which transmits the selected portion of the unabsorbed rays to an infrared detector 5. The infrared detector 5 converts the sensed rays into an electrical signal that represents the concentration of the target gas component which shows infrared absorption in the pass band wavelength of the bandpass filter 3.

The optical absorption of light due to the presence of the target component molecules in the measuring cell 1 is given by Beer's Law:

$$I(\lambda)=I_o(\lambda)e^{-ax} \quad (1)$$

a=k(λ)L k=(λ) wavelength dependent gas absorption coefficient

L=optical path length x=gas concentration

The absorption coefficients are dependent on wavelength and thus the appropriate absorption may be selected by choosing the optical filter characteristics carefully.

When there are three absorbing species in the measuring cell 1, equation (1) becomes:

$$I(\lambda)=I_o(\lambda)e^{-ax_1}e^{-bx_2}e^{-cx_3} \quad (2)$$

where now, a, b, and c represent the absorption coefficients of three different gases and $x_1$, $x_2$, and $x_3$ represent the corresponding concentrations of the three gases.

When the arguments of the exponentials are small, the following approximation of equation (2) may be used for three gases, for example:

$$I(\lambda)\equiv I_o(\lambda)[1-ax_1-bx_2-cx_3] \quad (3)$$

The prior art includes variations on the NDIR gas analyzer as shown in FIG. 1. For example, U.S. Pat. No. 5,429,805, issued to Uno, et al., discloses a Non-Dispersive Infrared Gas Analyzer Including Gas-Filled Radiation Source. The target gas component is enclosed in a sealed infrared radiation source which has a transmission window that transmits the infrared rays into the measuring cell. Thus, the infrared rays in the absorption center wavelength of the target gas component are removed in the radiation source.

Uno also discloses a motor with a rotating sector (chopper) which chops the infrared rays to interrupt the transmission of the rays into the measuring cell. The light is chopped because infrared detectors such as pyroelectric detectors respond to intermittent radiation. A portion of the infrared rays in the measuring cell is absorbed by the gas to be measured and is distributed over the wavelength outside the center absorption band of the target gas component. The target gas component shows a small absorption coefficient in the wavelength outside the center absorption band of the target gas.

Furthermore, Uno discloses an optical bandpass filter which is limited to the pass band of the target gas. The optical bandpass filter transmits a narrow wavelength range to the infrared detectors because the transmitted wavelength is the wavelength of the rays that were not absorbed by the target gas minus the center absorption wavelength that was absorbed in the infrared source.

The prior art also includes variations of the composition and texture of the lining of the measuring cell. For example, Wadsworth, et al., U.S. Pat. No. 5,453,620, discloses an optically reflective surface on the interior of the cell that has an irregular and constantly changing profile.

There is a large concentration of humidity present in the atmosphere in many environments in which NDIR gas analyzers are used. Water vapor may have an infrared absorption spectrum that overlaps that of the target gas component. There is also a large concentration of carbon dioxide present in the atmosphere in many environments in which NDIR gas analyzers are used. Carbon dioxide may have an infrared absorption spectrum that overlaps that of the target gas component. The prior art discussed does not contain adequate means for compensating for such humidity or carbon dioxide dependencies of the disclosed NDIR gas analyzers.

The prior art does not provide for optimization of the reflection of infrared rays in the sample gas measuring cell for improved illumination of multiple detectors.

Infrared detectors such as those used in NDIR gas analyzers are heat detectors, and thus the output of the analyzers are dependent on the temperature of the infrared detectors. The analyzers are also sensitive to the rate of temperature change. The prior art uses either active or passive devices for controlling temperature variations in NDIR gas analyzers.

Passive devices include heat sinks or thermal insulation but these devices cannot actively vary the temperature of the infrared detectors. Active devices allow a higher degree of control of the thermal environment of the infrared detectors but require control circuitry that is customized for the gas analyzer. The prior art uses such active devices as pulse width modulator temperature controllers that can produce large temperature gradients.

During the useful life of an infrared radiation source, the lamp degrades over time. The degradation causes the intensity of the light seen at the detector area of the NDIR gas analyzer to weaken over time. The prior art discussed does not disclose any method to compensate for such lamp aging effects.

Because the previously discussed problems greatly affect the sensitivity of NDIR gas analyzers, prior art NDIR gas analyzers are incapable of measuring at sensitivities in the parts per million range. There is a need for an NDIR gas analyzer that can measure the concentration of a target gas component in a sample gas in the parts per million range. There is also a need for an NDIR gas analyzer that compensates for the humidity present in the atmosphere of the device operating environment. Also, there is a need for an NDIR gas analyzer that can stabilize the temperature of the infrared detectors so as to reduce the temperature dependence of the device. Furthermore, there is a need for an NDIR gas analyzer that can compensate for the effects of infrared lamp degradation. Also, there is a need for an NDIR gas analyzer that has a sample gas cell with a reflective surface that maximizes optical throughout and uniformly illuminates the infrared detectors. There is also a need for an NDIR gas analyzer that compensates for the carbon dioxide present in the atmosphere of the device operating environment.

SUMMARY OF THE INVENTION

In accordance with the present invention, there is provided a non-dispersive gas analyzer that produces an output signal which represents the concentration of a target gas in a sample gas. A circuit for maintaining the temperature of the infrared detectors of the gas analyzer at a near constant temperature may also be provided. The gas analyzer may also include a circuit for controlling the intensity of the infrared light source such that the infrared light source emits infrared light at a near constant intensity over time. A method for measuring low concentrations of a target gas in a sample gas is also provided.

An advantage of the present invention is to provide a non-dispersive gas analyzer that compensates for the presence of interfering gases, such as humidity and carbon dioxide, when the concentration of a target gas is measured in a sample gas. According to another embodiment, the present invention provides the advantage of compensating for the temperature dependence of the analyzer by controlling the temperature of the infrared detectors. According to another embodiment of the present invention, the advantage of compensating for infrared light source degradation due to lamp aging effects is provided. Those advantages and benefits, and others, will become apparent from the Description of the Preferred Embodiments hereinbelow.

BRIEF DESCRIPTION OF THE DRAWINGS

In the accompanying drawings, there is shown preferred embodiments of the invention wherein like reference numerals are employed to designate like parts and wherein.

DETAILED DESCRIPTION OF THE INVENTION

Referring now to the figures for the purpose of illustrating a present preferred embodiment of the invention only and not for the purpose of limiting the same, the figures show a non-dispersive temperature compensated infrared gas analyzer having atmospheric humidity compensation and atmospheric carbon dioxide compensation which is resistant to lamp aging.

Figure 2A:
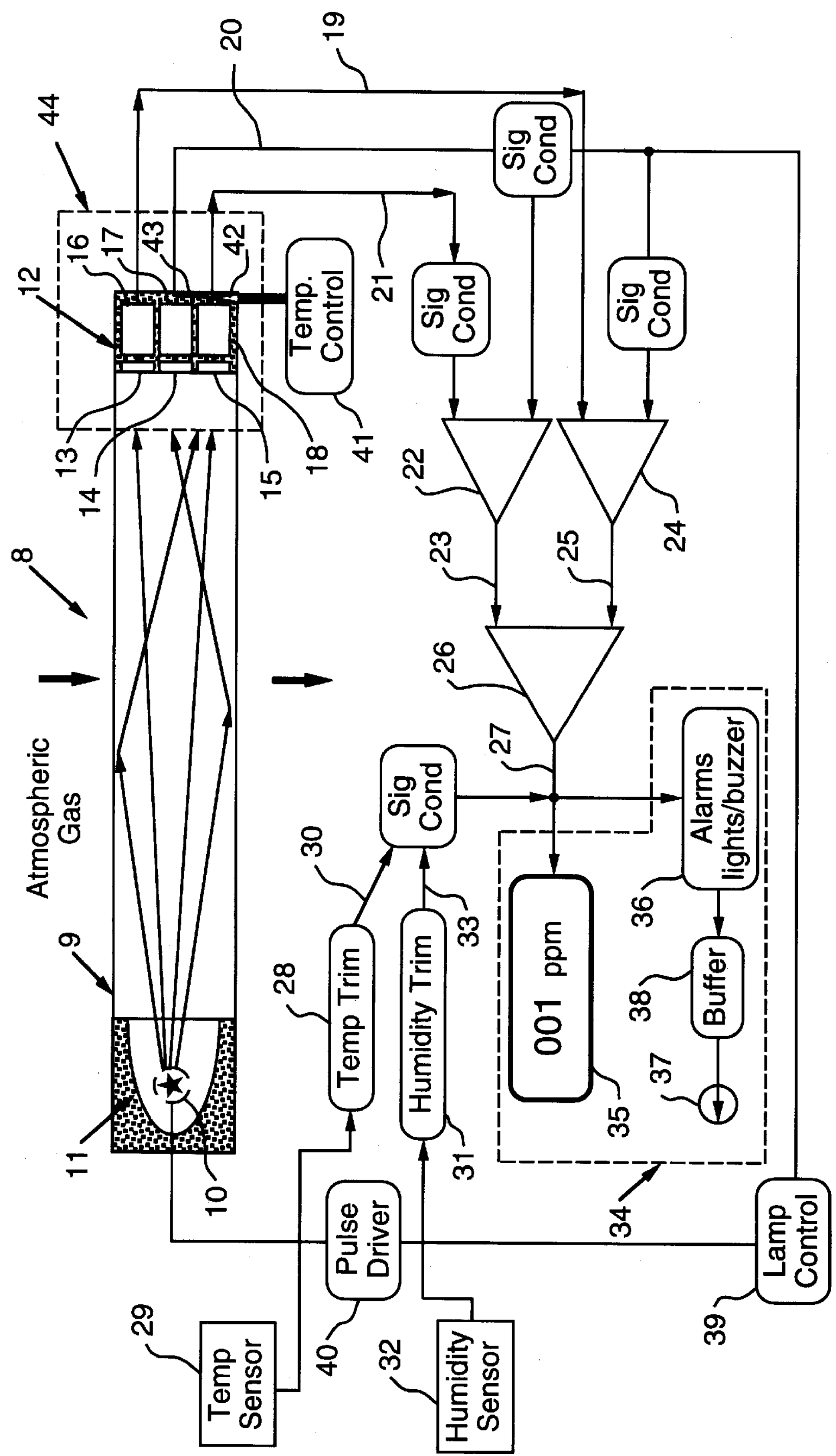
FIG. 2A is a functional layout of a preferred embodiment of the non-dispersive infrared gas analyzer of the present invention.

More particularly and with reference to FIG. 2A, a functional layout of a preferred embodiment of the present invention is shown. The NDIR gas analyzer is generally depicted as 8. The analyzer includes a sample gas measuring cell 9, which has an infrared light source 10 located at one end of the sample gas measuring cell 9 and is positioned such that infrared rays emitted by the infrared source 10 are emitted into the sample gas measuring cell 9. A parabolic reflector 11 reflects some of the infrared rays emitted by the infrared source 10 into the sample gas measuring cell 9.

Figure 2B:
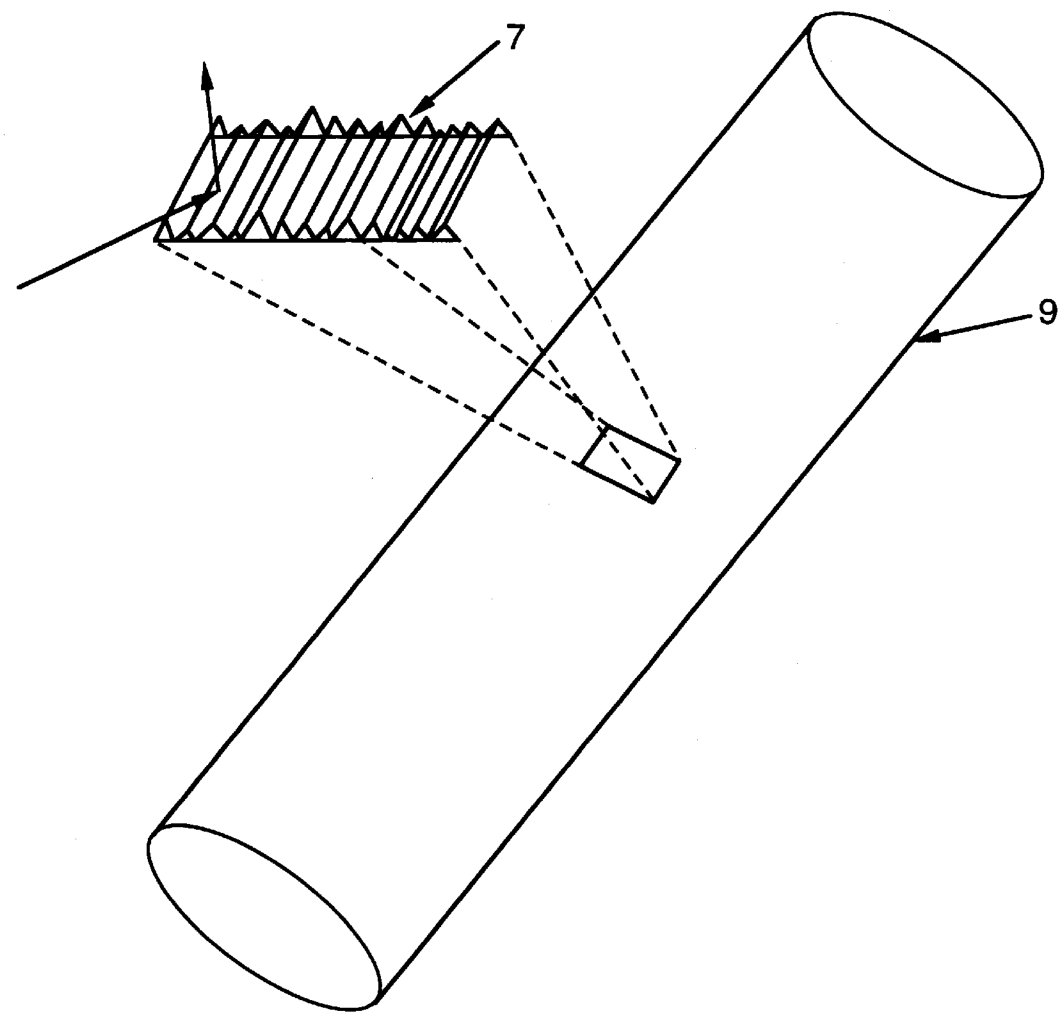
FIG. 2B is a magnified view of the striated inside walls of a sample gas measuring cell.

The sample gas measuring cell 9 can be constructed of a reflective material such as aluminum. The sample gas measuring cell 9 can be of any shape that is practicable for reflecting infrared light, such as conical, cylindrical, or square. In a preferred embodiment of the present invention, the inside walls of the sample gas measuring cell 9 are striated with longitudinal grooves 7, as seen in FIG. 2B, that reflect and diffuse the infrared light along the direction of the path of the light, while reducing backscatter of the rays. That achieves low loss transmission of infrared light to an infrared detection mounting block 12. The mounting block 12 is located at an end of the sample gas measuring cell 9 that is opposite the end where the infrared source 10 is located. Such low loss transmission of infrared light due to the reduction of backscatter of rays has not been realized in the prior art, such as Wadsworth, et al., U.S. Pat. No. 5,453,620. The striations formed on the inside of the sample gas measuring cell 9 can be created by, e.g., passing abrasive materials through the cell during manufacture. Alternatively, flexible reflective tape on which longitudinal striations are formed may be used to line the sample gas measuring cell 9.

The infrared detection mounting block 12 is preferably comprised of three single bandpass filters: a carbon dioxide bandpass filter 13, a reference bandpass filter 14, and a target gas and carbon dioxide bandpass filter 15. The infrared detection mounting block 12 preferably further comprises three infrared detectors: a carbon dioxide infrared detector 16, a reference infrared detector 17, and a target gas and carbon dioxide infrared detector 18. The detectors 16, 17, and 18 are located adjacent to the bandpass filters 13, 14, and 15, respectively. The infrared detection mounting block 12 may be constructed of a material that possesses high thermal conductivity, such as aluminum. The infrared detection mounting block 12 can also be surrounded by a thermally insulating compound, e.g. RTV silicone, to ensure thermal isolation of the infrared detector mounting block 12 from the environment.

One type of infrared detector that may be used in the detection block 12 is a pyroelectric detector, which may be operated without cooling, is inexpensive, and has excellent sensitivity in detecting infrared radiation at certain wavelengths, e.g., in the 4 to 5 micron wavelength range. However, it can be understood by those skilled in the art that many types of infrared detectors may be used to achieve the same results, including semiconductor-based infrared detectors or thermal-type detectors.

Atmospheric gas enters and passes through the sample gas measuring cell 9 through holes or perforations in the cell, and the target gas component of the sample gas absorbs the infrared rays at a characteristic wavelength, carbon dioxide absorbs the infrared rays at a characteristic wavelength, and water vapor absorbs the infrared rays at a characteristic wavelength. The unabsorbed rays at the above characteristic wavelengths are passed by the respective bandpass filters 13, 14, and 15 to the detectors 16, 17, and 18. The carbon dioxide infrared detector 16 produces an electrical signal 19 that is characteristic of the concentration of carbon dioxide in the sample gas. The reference infrared detector 17 produces an electrical signal 20 that is characteristic of the concentration of the infrared absorption of the water vapor in the sample gas. The target gas and carbon dioxide infrared detector 18 produces an electrical signal 21 that is characteristic of the concentration of the target gas and carbon dioxide in the gas sample. Electrical signals 19, 20, and 21 are conditioned and signals 20 and 21 are input to an operational amplifier 22, which subtracts the reference signal 20 from the target gas and carbon dioxide signal 21 to produce an intermediate signal 23, the voltage value of which is not dependent on water vapor. The signals 19 and 20 are input to an operational amplifier 24, which subtracts the reference signal 20 from the carbon dioxide signal 19 to produce an intermediate signal 25.

The intermediate signal 25 is subtracted from the intermediate signal 23 by an operational amplifier 26 to produce an output signal 27. The voltage value of the output signal 27 is thus proportional to the concentration of the gas component to be measured and does not depend on the concentration of carbon dioxide or water vapor in the sample gas.

Temperature changes at the detectors affect the voltage value of the output signal 27, which is given as:

$$V_0 30\ a(T-T_0)+b\ dT/dt \tag{4}$$

where T is the temperature at the detectors obtained from a temperature control 41, $T_0$ is the temperature at the detector when the zero adjustment was made at steady temperature, and $V_0$ is a part that is not affected by temperature. Temperature sensor 29 senses the ambient temperature of the gas analyzer 8. The residual temperature trim circuit 28 adds residual temperature trim signal 30 that is given by $$V_1-a(T-T_0) \tag{4a}$$

to the output signal 27. Thus, the residual temperature trim signal 30 helps to eliminate the portion of the non-optical thermal signal which is linear in the temperature.

An absolute humidity trim circuit 31 uses a voltage proportional to the relative humidity as sensed by a humidity sensor 32 to produce an absolute humidity trim signal 33, the voltage of which is proportional to the relative concentration of water vapor. The absolute humidity trim signal 33 adjusts the output signal 27 to compensate for any residual water sensitivity that was not removed after the two stages of operational amplifiers. This residual water sensitivity may not have been removed because of variations in bandpass filter characteristics that can be attributed to the manufacturing process of the filters.

Relative humidity is a measure of the amount of water vapor in the atmosphere relative to the maximum water vapor that the atmosphere can carry at a given temperature. The equation that covers the temperature variation of the maximum water vapor is given by the Clausius-Clapeyron equation:

$$P_{H_2O}=P_o l^{-L/RT} \tag{5}$$

$P_{H2O}$ is the partial pressure of water $P_o$ is a known constant

L is the latent heat of evaporation

R is the universal gas constant

T is the temperature

The concentration of water vapor at a relative humidity of $R_H$ at a given temperature T is given by:

$$x_H = \frac{P_{H_2O}(T)\cdot R_H}{P_{atm}} \tag{6}$$

An evaluation of the temperature dependence of the concentration shows that for a limited range of temperature near the operating temperature of the sample gas cell, the temperature dependence may be linearized such that:

$$x_H = \frac{P_{H_2O}(T)\cdot R_H}{P_{atm}} \cong \left[\frac{P_{H_2O}(T_O)}{P_{atm}} - \beta(T-T_O)\right]\cdot R_H \tag{7}$$

β is the temperature coefficient β is approximately 5% per degree Celsius under the conditions of operation in a preferred embodiment of the present invention and therefore a temperature sensitive amplifier was added to the absolute humidity trim circuit 31 to compensate for the temperature sensitivity β.

After the output signal 27 is adjusted by the residual temperature trim circuit 28 and the absolute humidity trim circuit 31, it is input to an output display circuit 34. The output display circuit 34 may contain an LCD display 35, LED/buzzer alarms 36, or an analog voltage output 37 that is buffered by an output buffer 38. Those skilled in the art will recognize that other output devices may be connected to the output signal 27, such as a voltage monitor output or other combinations of digital or analog displays.

An active lamp control circuit 39 receives the reference signal 20 and calculates the change in the reference signal 20 as a consequence of light changes due to variations in the optical path, such as light source aging, sample gas cell degradation, or changes in absorption in the passband of the reference detector. The active lamp control circuit 39 ensures that a constant level of light is present at the reference detector 17 by controlling a pulse driver 40 to adjust the power of each pulse to the infrared source 10. The pulse driver 40 is preferably an operational amplifier oscillator circuit that produces a square wave pulse at the approximate frequency of 1.5 Hz.

Figure 3:
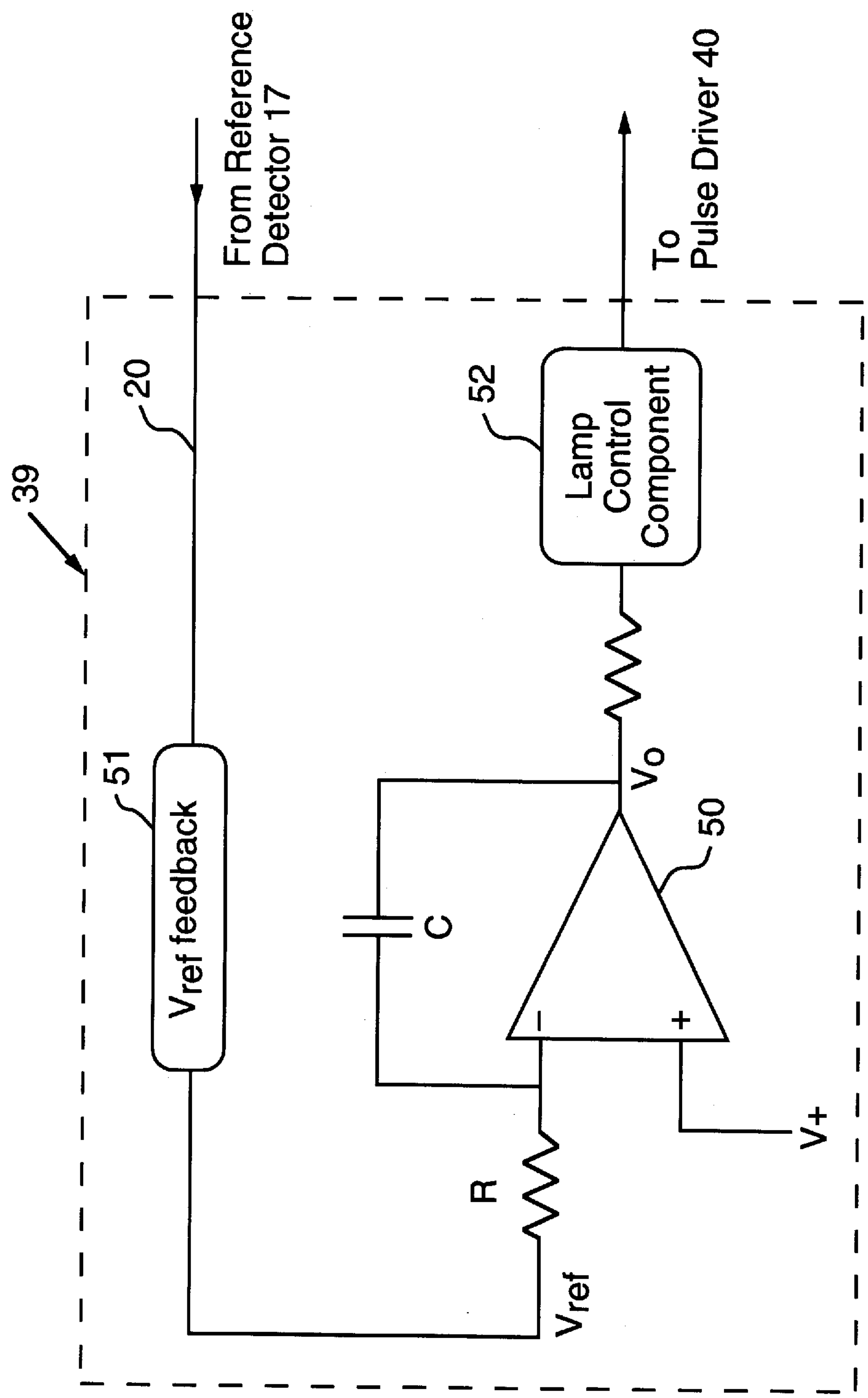
FIG. 3 is a simplified view of an active lamp control circuit of a preferred embodiment of the present invention.

A simplified diagram of the lamp control circuit 39 is shown in FIG. 3. An operational amplifier 50 acts as an integrator and controls the light output within a limited range to the pulse driver 40. The reference signal 20, which is produced by the reference detector 17, feeds back through a reference feedback circuit 51 into the operational amplifier 50, which provides a control signal to a lamp control component 52 of the lamp control circuit 39. The voltage value of the reference signal 20 is indicated as $V_{ref}$.

The response of the operational amplifier 50 may be given as:

$$\frac{dV_o}{dt} = \frac{(V_+ - V_{ref})}{RC} \tag{8}$$

With feedback from the feedback circuit 51, the operational amplifier may be characterized as:

$$V_+ = V_{ref} \frac{dV_o}{dt} = 0 \tag{9}$$

The output of the reference detector 17, reference signal 20 ($V_{ref}$), is held at the constant value $V_+$.

Because the reference detector 17 is chosen such that it has the same sensitivity to water vapor as the target gas and carbon dioxide detector 18, a decrease in the reference signal 20 produces a corresponding increase in light intensity and helps to compensate for water vapor absorption seen by the target gas and carbon dioxide detector 18 when water vapor is present in the sample gas cell 9.

Returning now to FIG. 2A, a temperature control circuit 41 is an active circuit which controls a detector heater 42 by raising or lowering the electrical current supplied to the heater 42 proportional to deviations in temperature of the detectors 16, 17, and 18. A thermistor 43 measures the temperature of the detectors 16, 17, and 18 and feeds the measurement back to the temperature control circuit 41. The detectors 16, 17, and 18, the infrared detector mounting block 12, the thermistor 43, and the detector heater 42 comprise an optical detector head 44.

The equations governing the thermal response of the detectors 16, 17, and 18 can be written such that the signal S developed from a detector can be broken into two parts. One part is due to light falling on the detector and the other part is due to the other temperature changes of the detector:

$$S = S_{optical} + S_{thermal} \tag{10}$$

S is the overall signal $S_{optical}$ is the signal due to light $S_{thermal}$ is the signal due to non-optical temperature changes The gas detection capability of the detector is compromised if the thermal portion of the signal becomes comparable the optical portion. The thermal portion of the signal may be described as:

$$S_{thermal} \equiv c_o T + c_1 \frac{dT}{dt} \tag{11}$$

where T is the temperature

In the case of a single detector, it is desirable to have the coefficients $c_0$ and $c_1$ as small as possible to minimize the thermal signal. When more than one detector is used, the coefficients $c_0$ and $c_1$ may be matched to reduce or eliminate the thermal signal.

$$S_{th1} \equiv c_{01} T + c_{11} \frac{dT}{dt} \tag{12}$$

$$S_{th2} \equiv c_{02} T + C_{12} \frac{dT}{dt} \tag{13}$$

$$S_{th2} - S_{th1} = (c_{02} - c_{01})T + (c_{12} - c_{11}) \frac{dT}{dt} \tag{14}$$

$$S_{th2} - S_{th1} = 0 \text{ if } c_{02} = c_{01} \text{ and } c_{12} = c_{11} \tag{15}$$

Figure 4:
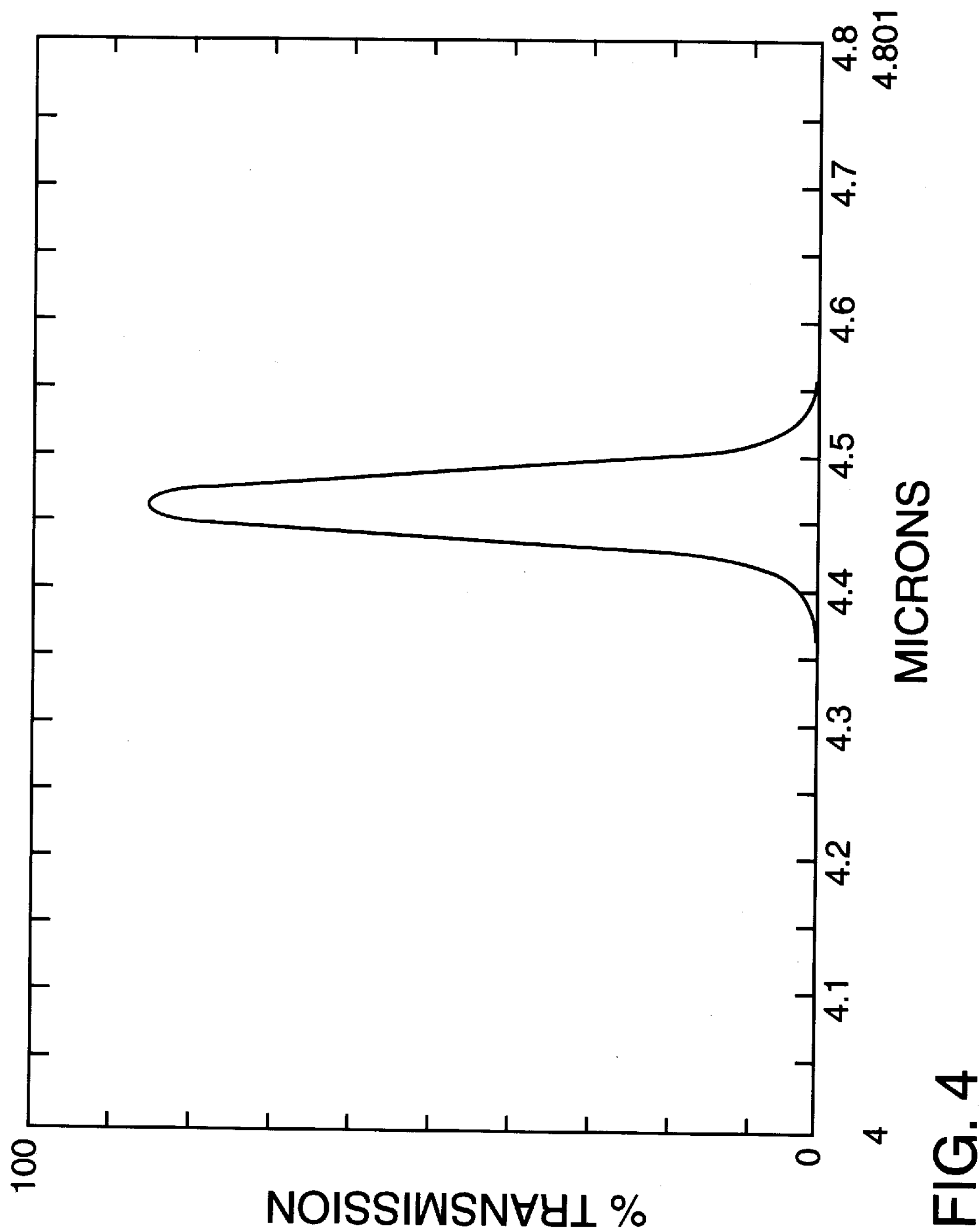
FIG. 4 is a graph of the pass band for the target gas bandpass filter of a preferred embodiment of the present invention.

A description of an example of a non-dispersive gas analyzer designed according to the teachings of the present invention follows. The gas analyzer was designed to measure the concentration of nitrous oxide ($N_2O$) in a sample gas. The target gas and carbon dioxide bandpass filter 15 and the target gas detector 23 were designed to optimally pass and detect infrared rays unabsorbed by nitrous oxide at its peak transmission wavelength. FIG. 4 shows a preferred response of a nitrous oxide bandpass filter designed to pass the unabsorbed infrared rays at a wavelength of nitrous oxide absorption.

The gas analyzer must be able to measure the concentration of nitrous oxide in the parts per million range and therefore must compensate for the carbon dioxide and water vapor present in the sample gas. In the following equations, nitrous oxide is represented by N, carbon dioxide by C, and water vapor by H. Thus, Beer's law from equation (3) may be written as:

$$I^N(\lambda) = I_o^N(\lambda) l^{-a_N x_N} l^{-b_N x_C} l^{-c_N x_H} \tag{16}$$

$$a_N = k_N(\lambda) L \tag{17}$$

$$I^C(\lambda) = I_O^C(\lambda) l^{-a_C x_N} l^{-b_x x_C} L^{-c_C x}{}_N \tag{18}$$

$$a_C = k_C(\lambda) L \tag{19}$$

$$I^R(\lambda) = I_o^R(\lambda) l^{-a_C x_N} l^{-b_C x_C} l^{-C_C x_N} \tag{20}$$

$$a_R = k_R(\lambda) L \tag{21}$$

Equations (16)–(21) may be linearized as:

$$I^N(\lambda) \equiv I_o^N[1 - a_N x_N - b_N x_C - c_N x_H] \tag{22}$$

$$I^R(\lambda) \equiv I_o^R[1 - a_R x_N - b_R x_C - c_R x_H] \tag{23}$$

$$I^C(\lambda) \equiv I_o^C[1 - a_C x_N - b_C x_C - c_C x_H] \tag{24}$$

Equations (22)–(24) may also be represented in vector-matrix form as:

$$\begin{pmatrix} I^N(\lambda) \\ I^C(\lambda) \\ I^R(\lambda) \end{pmatrix} \equiv \begin{pmatrix} I_o^N(\lambda) & 0 & 0 \\ 0 & I_o^C(\lambda) & 0 \\ 0 & 0 & I_o^R(\lambda) \end{pmatrix} \left[ 1 - \begin{pmatrix} a_N & b_N & c_N \\ a_C & b_C & c_C \\ a_R & b_R & c_R \end{pmatrix} \begin{pmatrix} x_N \\ x_C \\ x_H \end{pmatrix} \right] \tag{25}$$

Figure 5:
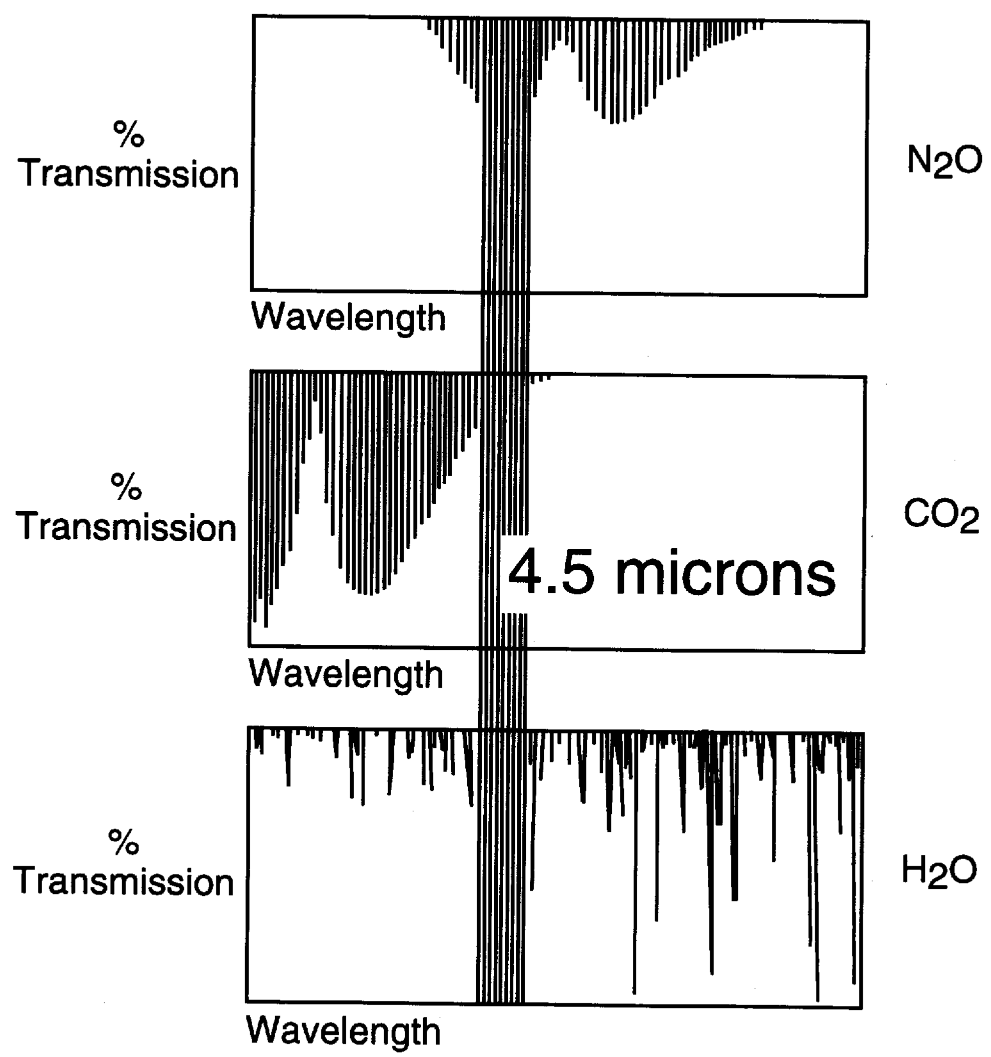
FIG. 5 is a graph illustrating the absorption spectrum of a target gas, humidity and carbon dioxide.
Figure 6:
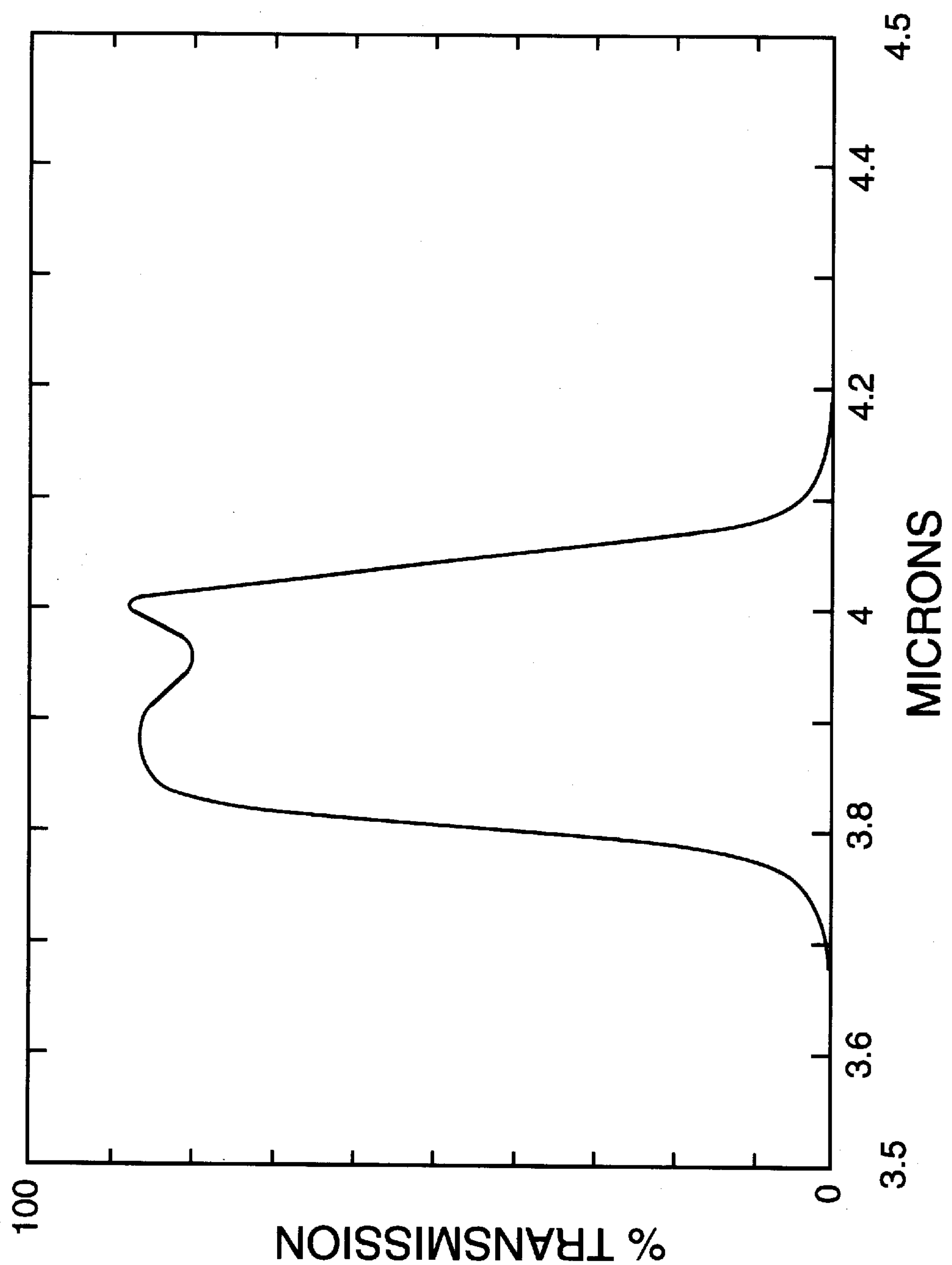
FIG. 6 is a graph of the pass band for the reference bandpass filter of a preferred embodiment of the present invention.
Figure 7:
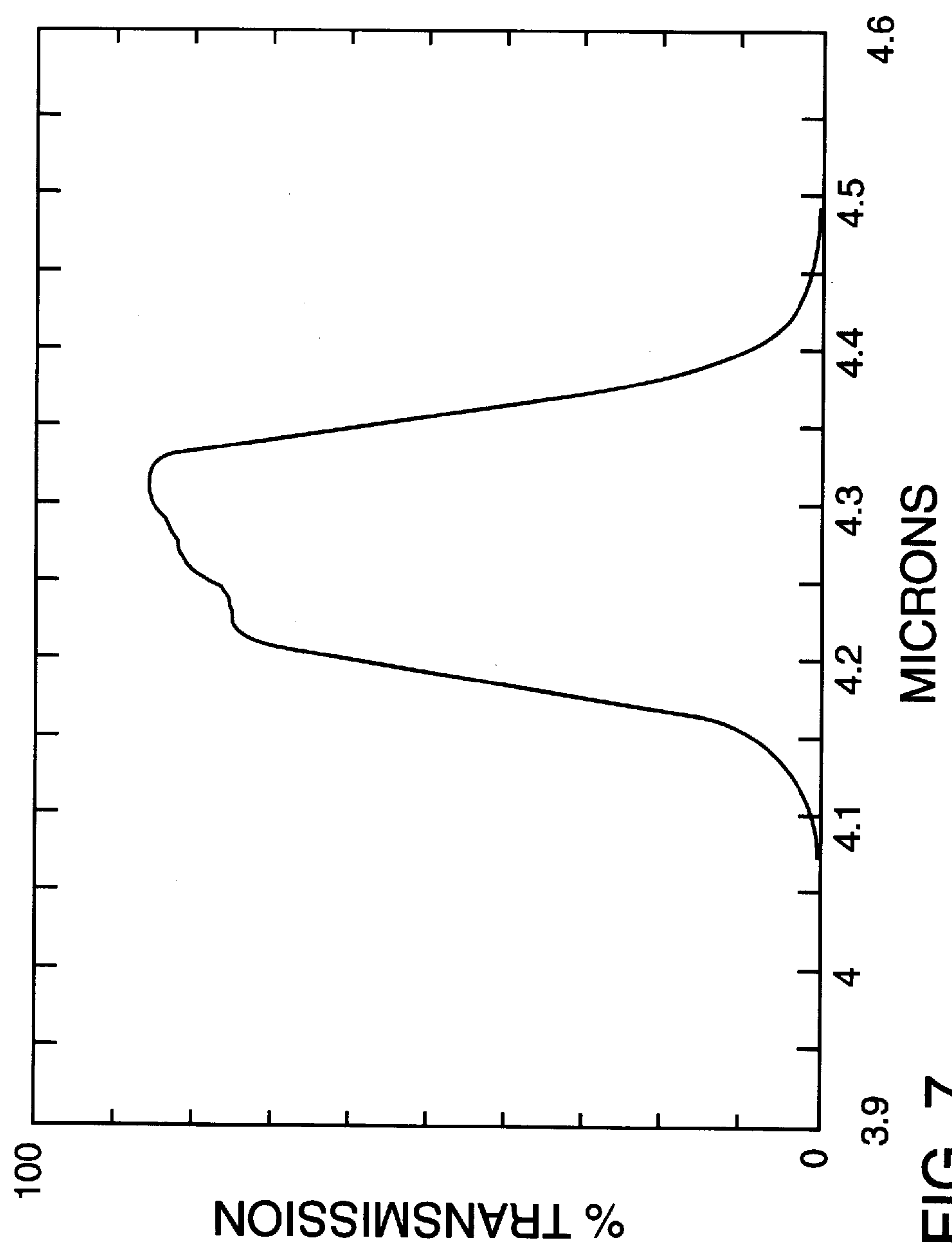
FIG. 7 is a graph of the pass band for the carbon dioxide bandpass filter of a preferred embodiment of the present invention.

FIG. 5 shows the percent transmission of infrared light for the identified gas on the y-axis and the wavelength on the x-axis. The location of the primary absorption band of nitrous oxide, shown as a shaded column in the figure, corresponds to some absorption by carbon dioxide and water. Therefore, without compensation, the gas analyzer would respond to carbon dioxide, water, and nitrous oxide. To subtract the response due to water vapor from the outputted signal, the reference bandpass filter 14 must be designed to have a passband at which no absorption by nitrous oxide occurs and absorption by water is matched with that at the selected passband shown in FIG. 4. FIG. 6 shows the response of a preferred reference filter. Also, to subtract the response due to carbon dioxide from the outputted signal, the carbon dioxide bandpass filter 13 must be designed to pass wavelengths associated with carbon dioxide absorption, but does not transmit substantially at wavelengths associated with nitrous oxide absorption. FIG. 7 shows the response of a preferred carbon dioxide filter that is of one type that is commonly commercially available.

The three detectors produce voltages that are proportional to the light intensity signals received at each of the three detectors. These voltages are given as:

$$V^N = V_o^N + \alpha_N[1 - a_N x_N - b_N x_C - c_N x_H] \quad (26)$$

$$V^R = V_o^R + \alpha_R[1 - a_R x_N - b_R x_C - c_R x_H] \quad (27)$$

$$V^C = V_o^C + \alpha_C[1 - a_C x_N - b_C x_C - c_C x_H] \quad (28)$$

where:

$\alpha_i$=voltage proportionality factors

Figure 1:
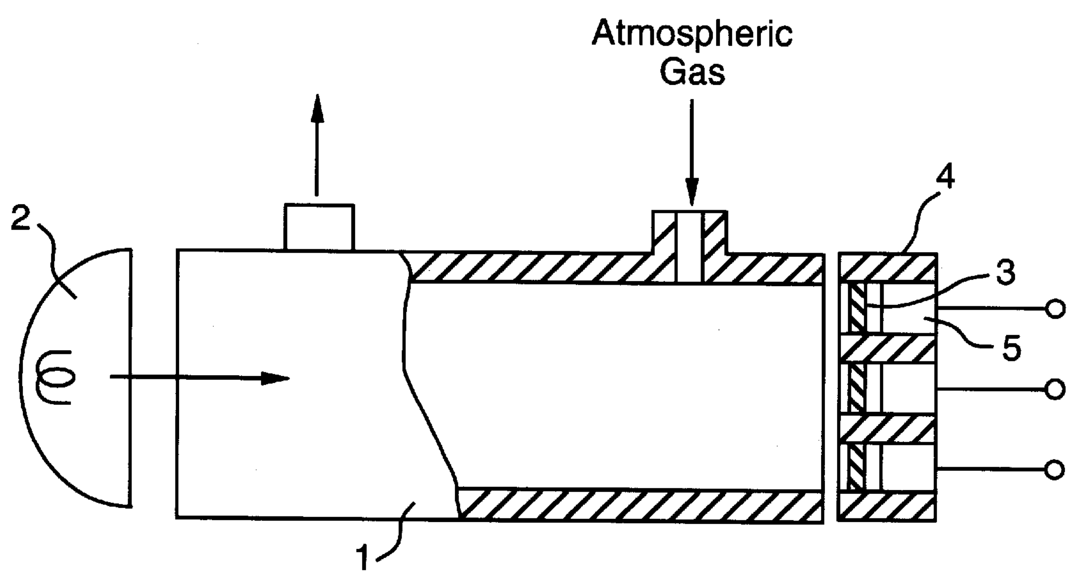
FIG. 1 is a view of a typical prior art non-dispersive infrared gas analyzer.

From those voltages, signals are derived by subtraction of the reference voltage (signal 20 in FIG. 1) from the N and C voltages (signals 21 and 19, respectively, in FIG. 2). Those signals are given as:

$$S^N = \frac{V^N}{\alpha_N} - \frac{V^R}{\alpha_R} = S_o^N - (a_N - a_R)x_N - (b_N - b_R)x_C - (c_N - c_R)x_H \quad (29)$$

$$S^C = \frac{V^C}{\alpha_C} - \frac{V^R}{\alpha_R} = S_o^C - (a_C - a_R)x_N - (b_C - b_R)x_C - (c_C - c_R)x_H \quad (30)$$

The absorption coefficients depend on the optical wavelengths selected using the appropriate bandpass filters. In the case of a nitrous oxide gas analyzer, the filter characteristics are given such that the following relationships hold:

$$c_N \cong c_R \quad \text{water response of reference channel matches nitrous channel} \quad (31)$$

$$a_R \cong b_R \cong 0 \quad \text{reference has negligible response to nitrous or carbon dioxide} \quad (32)$$

$$\frac{b_N}{b_C} << 1 \quad CO_2 \text{ channel is much more sensitive to } CO_2 \text{ than to } N_2O \quad (33)$$

The water response and nitrous oxide sensitivity of the carbon dioxide bandpass filter are negligible with respect to the carbon dioxide sensitivity of the carbon dioxide bandpass filter, such that the following relationships hold:

$$(c_C - c_R)x_H << (a_C - a_R)x_N << (b_C - b_R)x_C \quad (34)$$

$$\text{i.e. } (c_C - c_R)x_H << a_C x_N << b_C x_C \quad (35)$$

The signal equations from equations (29) and (30) thus can be simplified to:

$$S_N = S_o^N - a_N x_N - b_N x_C \quad (36)$$

$$\text{and } S^C = S_o^C - a_C x_N - b_C x_C \quad (37)$$

This allows for the subtraction of the carbon dioxide signal to produce a difference signal $D^N$ which varies linearly only to the concentration of $N_2O$. $D^N$ is thus given as:

$$D^N = S^N - \frac{b_N}{b_C} S^C = -\left( a_N - \frac{b_N}{b_C} a_C \right) x_N + D_o^N \quad (38)$$

where $$D_o^N = \left( S_o^N - \frac{b_N}{b_C} S_o^C \right).$$

$D^N$ then represents a signal which varies linearly to the $N_2O$ concentration $X_N$ in the presence of water vapor and carbon dioxide. In our instrument, since $b_N/b_C<<1$, the sensitivity of the nitrous difference signal $D^N$ of equation (38) is controlled by the nitrous absorption of the nitrous channel $a_N$.

Figure 8A:
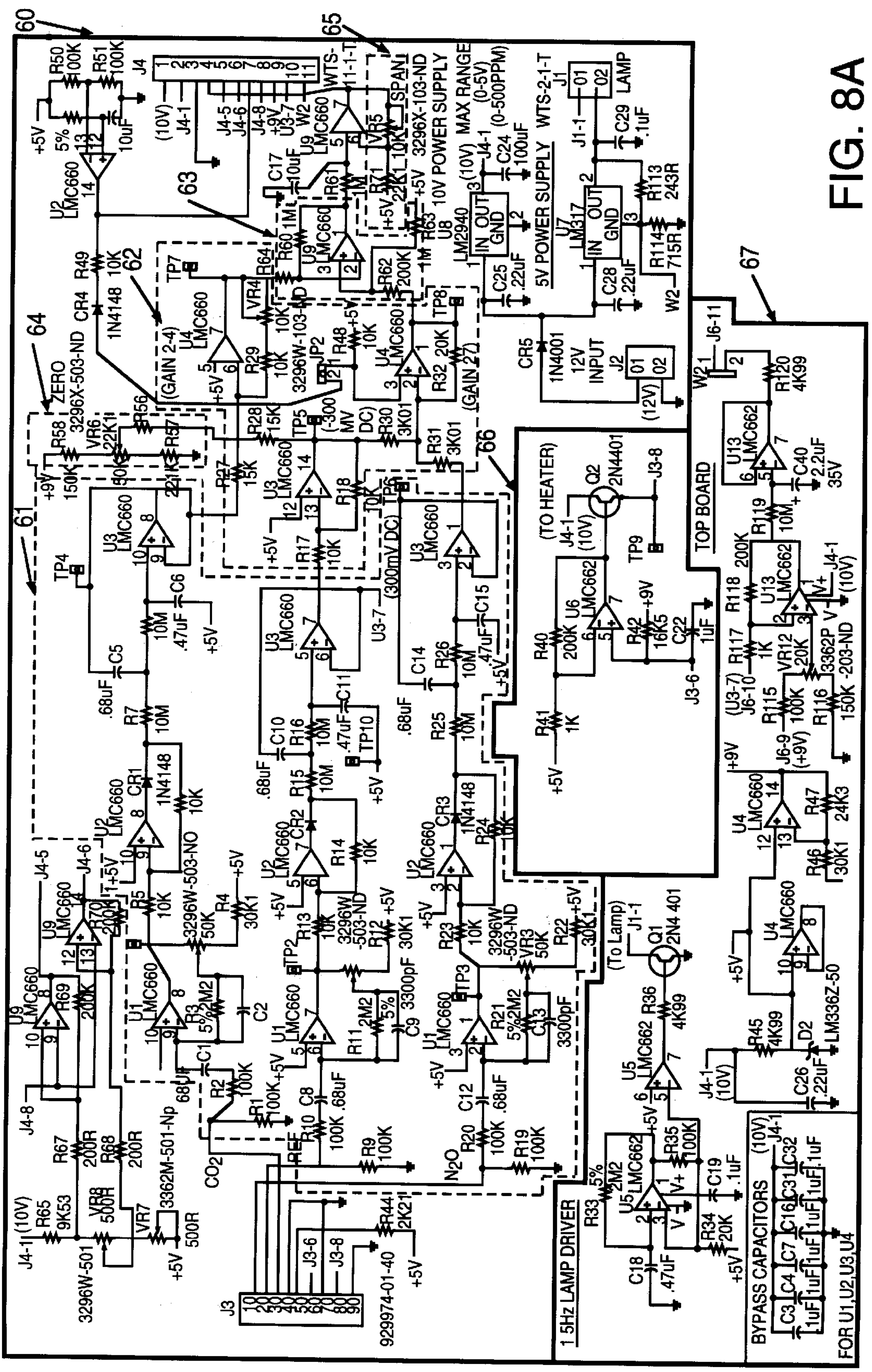
FIG. 8A is a partial view of an electrical circuit implementation of a preferred embodiment of the present invention.
Figure 8B:
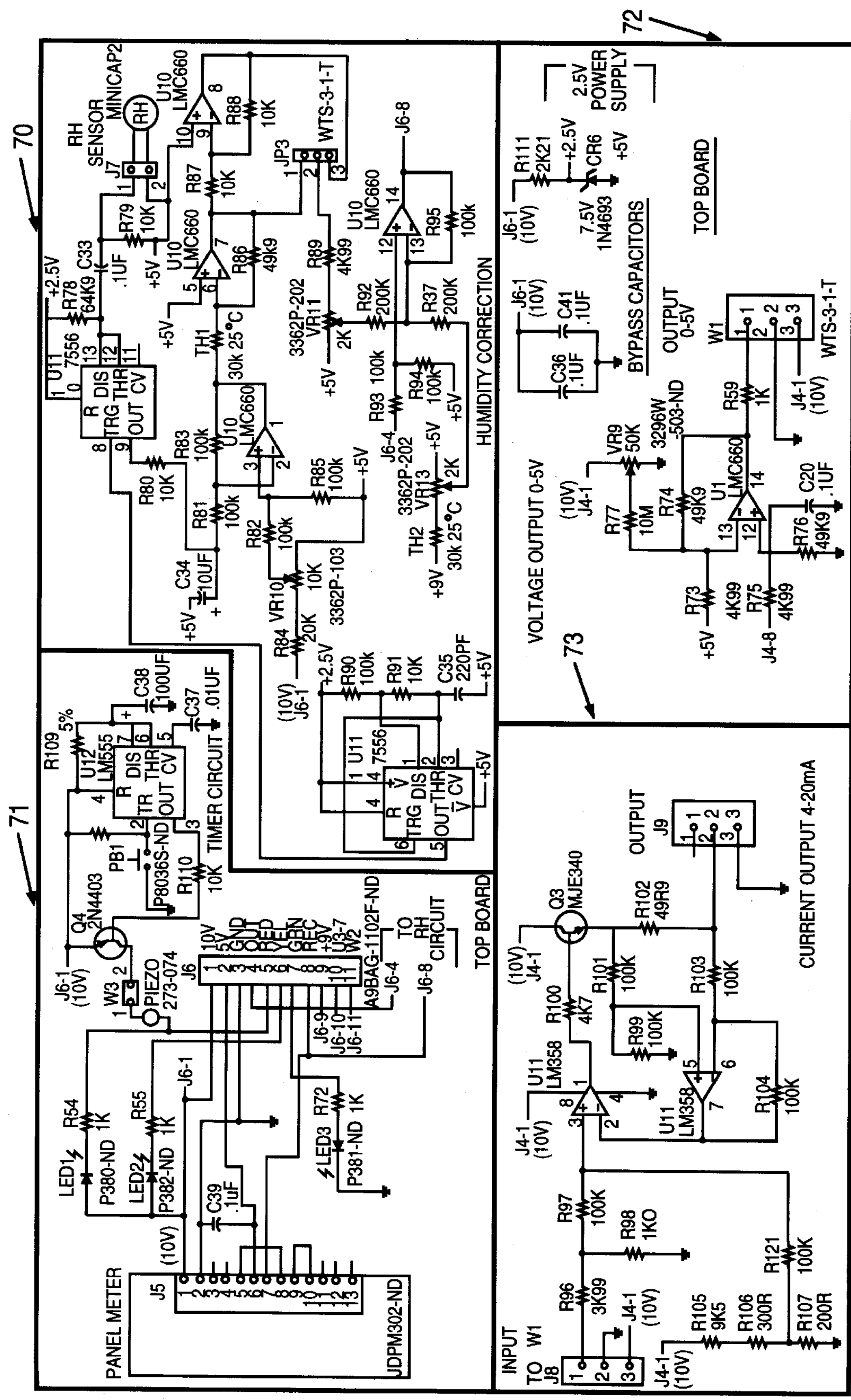
FIG. 8B is a partial view of an electrical circuit implementation of a preferred embodiment of the present invention.

FIGS. 8A and 8B are views of circuit layouts of an implementation of a preferred embodiment of a nondispersive gas analyzer that measures the concentration of nitrous oxide in a sample gas. The analyzer was constructed according to the principles embodied in FIGS. 2–7 and the accompanying explanations. FIG. 8A shows a main signal channel circuit 60. The main signal channel circuit 60 performs amplification and differencing of the outputs of the three infrared detectors. An amplification circuit 61 of the main signal channel circuit 60 converts the optical signal produced by each detector into a level electrical signal. A reference subtraction circuit 62 of the main signal channel circuit 60 subtracts the signal representing the concentration of water vapor present in the sample gas, the light intensity in the passband of the reference detector, and any noise that is present from the carbon dioxide detector signal and the target gas and carbon dioxide signal. A carbon dioxide subtraction circuit 63 of the main signal channel circuit 60 subtracts the signal representing the concentration of carbon dioxide present in the sample gas from the target gas and carbon dioxide signal.

The main signal channel circuit 60 also has a zero calibration circuit 64 which is used to adjust the gas analyzer to its zero setting. Calibration to the zero setting is accomplished by adjusting a potentiometer in the zero calibration circuit 64 until the analyzer display outputs a "0" reading in an environment that has no nitrous oxide present.

The main signal channel circuit 60 also has a span calibration circuit 65 which is used to calibrate the span of the analyzer in the presence of a known concentration of nitrous oxide. The potentiometer of the span calibration circuit 65 is adjusted when the sample gas cell of the analyzer is filled with a known concentration of nitrous oxide.

FIG. 8A shows a heater control circuit 66 which is used to maintain a constant temperature of the optical detector head. This allows for the measurement of small optical signals at the detectors because the circuit minimizes the signal associated with the thermal sensitivity of the detectors. In the circuit configuration shown as used on the analyzer, the heater control circuit 66 can hold the temperature of the optical detector head within 0.01 degree Celsius of the desired temperature.

An active lamp control circuit 67 compensates for the degradation of the infrared light source by adjusting the intensity of the signal produced by the lamp driver.

A relative humidity trim circuit 70 is shown in FIG. 8B. The relative humidity trim circuit 70 compensates for variations in humidity response due to filter-to-filter variations. A small signal is added or subtracted to the output signal by the relative humidity trim circuit 70 to trim the humidity response.

An output display circuit 71 displays the outputted value of the nitrous oxide concentration of the sample gas in various forms. The output display circuit 71 in the embodiment shown uses LCD and LED displays and a buzzer.

A voltage output circuit 72 provides a 0–5 volt DC analog signal that is suitable for connection to a data logger or a centralized multipoint control/monitoring system. A current output circuit 73 provides a 4–20 mA output signal that can be used for data logging purposes.

The present invention provides solutions to the problem of non-dispersive infrared gas analyzers that are in use today that cannot measure the concentrations of a target gas in the parts per million range because of humidity and carbon dioxide concentrations present in a sample gas, light source degradation over time, and/or the thermal dependencies of optical detectors. It will be understood, however, that various changes in the details, materials, and arrangements of parts which have been herein described and illustrated to explain the nature of the invention may be made by those skilled in the art within the principle and scope of the invention as expressed in the appended claims.

What is claimed is:

1. An infrared gas analyzer for measuring low concentrations of nitrous oxide in a sample gas, comprising:

a gas sampling chamber having a first end and a second end;

an infrared light source located at said first end of said gas sampling chamber such that light produced by said infrared light source projects into said gas sampling chamber;

a power source for energizing said infrared light source;

a plurality of filters located at said second end of said gas sampling chamber, wherein one of said filters is a first bandpass filter for transmitting wavelengths of infrared light at an optimal wavelength for nitrous oxide and at a wavelength associated with carbon dioxide in the sample gas and wherein one of said filters is a second bandpass filter for transmitting wavelengths of infrared light at a wavelength associated with water;

a plurality of infrared detectors each responsive to one of said filters for producing a plurality of electrical signals representative of the amount of detected infrared light; and a circuit for combining said electrical signals to produce an output signal representative of the concentration of nitrous oxide independently of other gases in the sample gas.

2. The infrared gas analyzer of claim 1 further comprising means for controlling the intensity of said infrared light source, said means being responsive to one of said infrared detectors for producing a signal input to said power source such that said infrared light source emits infrared light at a substantially constant intensity over time.

3. The infrared gas analyzer of claim 1 wherein said power source produces pulses for energizing said infrared light source.

4. The infrared gas analyzer of claim 1 further comprising:

a temperature sensor responsive to the temperature of said infrared detectors; and means, responsive to said temperature sensor, for maintaining the temperature of said infrared detectors at a substantially constant value.

5. The infrared gas analyzer of claim 1 wherein said gas sampling chamber has a striated lining.

6. The infrared gas analyzer of claim 1 wherein said gas sampling chamber has a striated interior surface.

7. The infrared gas analyzer of claim 1 further comprising a second temperature sensor and a residual temperature trim circuit responsive to said second temperature sensor for modifying said output signal to compensate for large temperature variations of said infrared gas analyzer.

8. The gas analyzer of claim 1 further comprising a relative humidity sensor and an absolute humidity circuit responsive to said humidity sensor for modifying said output signal to compensate for any residual water sensitivity of said gas analyzer.

9. The infrared gas analyzer of claim 1 wherein one of said filters passes infrared light at a wavelength of approximately 4.5 microns, one of said filters passes infrared light at a wavelength of approximately 4 microns, and one of said filters passes infrared light at a wavelength of approximately 4.3 microns.

10. An infrared gas analyzer for measuring low concentrations of a target gas in a sample gas, comprising:

a gas sampling chamber having a first ends a second end and a striated lining;

an infrared light source located at said first end of said gas sampling chamber such that light produced by said infrared light source projects into said gas sampling chamber;

a power source for energizing said light source;

a filter located at said second end of said gas sampling chamber and responsive to a wavelength of absorption for the target gas;

an infrared detector responsive to said filter for producing an electrical signal representative of the concentration of the target gas; and means for controlling the intensity of said infrared light source, said means being responsive to said infrared detector for producing a signal input to said power source such that said infrared light source emits infrared light at a substantially constant intensity over time.

11. The infrared gas analyzer of claim 10 wherein said filter is a bandpass filter.

12. The infrared gas analyzer of claim 10 further comprising:

a temperature sensor responsive to the temperature of said infrared detector; and means, responsive to said temperature sensor, for maintaining the temperature of said infrared detector at a substantially constant value.

13. The infrared gas analyzer of claim 10 further comprising a second temperature sensor and a residual temperature trim circuit responsive to said second temperature sensor for modifying said output signal to compensate for large temperature variations of said infrared gas analyzer.

14. The infrared gas analyzer of claim 10 further comprising a relative humidity sensor and an absolute humidity circuit responsive to said humidity sensor for modifying said output signal to compensate for any residual water sensitivity of said gas analyzer.

15. An infrared gas analyzer for measuring low concentrations of a target gas in a sample gas, comprising:

a gas sampling chamber having a first end, a second end, and a striated lining;

means for producing infrared light and for projecting the infrared light into said first end of said gas sampling chamber;

a plurality of filters located at said second end of said gas sampling chamber;

a plurality of infrared detectors each responsive to one of said filters for producing a plurality of electrical signals representative of the amount of detected infrared light;

means for combining said electrical signals to produce an output signal representative of the concentration of the target gas;

a temperature sensor responsive to the temperature of said infrared detectors; and means, responsive to said temperature sensor, for maintaining the temperature of said infrared detectors at a substantially constant value.

16. The infrared gas analyzer of claim 15 wherein one of said filters is a bandpass filter which has a passband wavelength of approximately 4.3 microns.

17. The infrared gas analyzer of claim 16 wherein another of said filters is a bandpass filter which has a passband wavelength of approximately 4 microns.

18. The infrared gas analyzer of claim 15 wherein said means for producing infrared light includes an infrared light source and a power source producing pulses for energizing said light source.

19. The infrared gas analyzer of claim 15 further comprising a second temperature sensor and a residual temperature trim circuit responsive to said second temperature sensor for modifying said output signal to compensate for large temperature variations of said infrared gas analyzer.

20. The infrared gas analyzer of claim 15 further comprising a humidity sensor and a humidity circuit responsive to said humidity sensor for modifying said output signal to compensate for any residual water sensitivity of said gas analyzer.

21. The infrared gas analyzer of claim 15 wherein one of said filters passes infrared light at a wavelength of approximately 4.5 microns, one of said filters passes infrared light at a wavelength of approximately 4 microns, and one of said filters passes infrared light at a wavelength of approximately 4.3 microns.

22. An infrared gas analyzer for measuring the concentration of nitrous oxide in a sample gas, comprising:

a gas sampling chamber having a first end, a second end, and a lining that is longitudinally striated;

an infrared light source located at said first end of said gas sampling chamber such that light produced by said infrared light source projects into said gas sampling chamber;

a power source for energizing said infrared light source;

a first bandpass filter, a second bandpass filter, and a third bandpass filter, said bandpass filters located at said second end of said gas sampling chamber;

a first infrared detector responsive to said first bandpass filter for producing a first electrical signal representative of the amount of detected infrared light at a wavelength corresponding to an absorption wavelength of water;

a second infrared detector responsive to said second bandpass filter for producing a second electrical signal representative of the amount of detected infrared light at a wavelength corresponding to an absorption wavelength of carbon dioxide;

a third infrared detector responsive to said third bandpass filter for producing a third electrical signal representative of the amount of detected infrared light at a wavelength corresponding to an absorption wavelength of nitrous oxide;

an electrical circuit for combining said first electrical signal, said second electrical signal, and said third electrical signal to produce an output signal representative of the concentration of the nitrous oxide independently of the carbon dioxide and water in the sample gas;

a temperature sensor responsive to the temperature of said infrared detectors;

a circuit, responsive to said temperature sensor, for maintaining the temperature of said infrared detectors at a substantially constant value; and a control circuit for controlling the intensity of said infrared light source, said control circuit being responsive to one of said infrared detectors for producing a signal input to said power source such that said infrared light source emits infrared light at a substantially constant intensity over time.

23. The infrared gas analyzer of claim 22 wherein said first bandpass filter has a passband wavelength of approximately 4 microns.

24. The infrared gas analyzer of claim 23 wherein said second bandpass filter has a passband wavelength of approximately 4.3 microns.

25. The infrared gas analyzer of claim 24 wherein said third bandpass filter has a passband wavelength of approximately 4.5 microns.

26. The infrared gas analyzer of claim 25 wherein said infrared detectors are pyroelectric detectors.

27. The infrared gas analyzer of claim 22 wherein said gas sampling chamber is constructed of a material selected from the group consisting of aluminum and gold.

28. The infrared gas analyzer of claim 22 further comprising a second temperature sensor and a residual temperature trim circuit responsive to said second temperature sensor for modifying said output signal to compensate for large temperature variations of said infrared gas analyzer.

29. The infrared gas analyzer of claim 28 further comprising a relative humidity sensor and an absolute humidity circuit responsive to said humidity sensor for modifying said output signal to compensate for any residual water sensitivity of said gas analyzer.

30. The infrared gas analyzer of claim 22 wherein said analyzer measures concentrations of nitrous oxide at levels of parts per million.

31. An infrared gas analyzer for measuring low concentrations of a target gas in a sample gas, comprising:

a gas sampling chamber having a first end, a second end, and a striated interior surface;

an infrared light source located at said first end of said gas sampling chamber such that light produced by said infrared light source projects into said gas sampling chamber;

a power source for energizing said light source;

a filter located at said second end of said gas sampling chamber and responsive to a wavelength of absorption for the target gas;

an infrared detector responsive to said filter for producing an electrical signal representative of the concentration of the target gas; and means for controlling the intensity of said infrared light source, said means being responsive to said infrared detector for producing a signal input to said power source such that said infrared light source emits infrared light at a substantially constant intensity over time.

32. The infrared gas analyzer of claim 31 wherein said filter is a bandpass filter.

33. The infrared gas analyzer of claim 31 further comprising:

a temperature sensor responsive to the temperature of said infrared detector; and means, responsive to said temperature sensor, for maintaining the temperature of said infrared detector at a substantially constant value.

34. The infrared gas analyzer of claim 31 further comprising a second temperature sensor and a residual temperature trim circuit responsive to said second temperature sensor for modifying said output signal to compensate for large temperature variations of said infrared gas analyzer.

35. The infrared gas analyzer of claim 31 further comprising a relative humidity sensor and an absolute humidity circuit responsive to said humidity sensor for modifying said output signal to compensate for any residual water sensitivity of said gas analyzer.

36. An infrared gas analyzer for measuring low concentrations of a target gas in a sample gas, comprising:

a gas sampling chamber having a first end, a second end, and a striated interior surface;

means for producing infrared light and for projecting the infrared light into said first end of said gas sampling chamber;

a plurality of filters located at said second end of said gas sampling chamber;

a plurality of infrared detectors each responsive to one of said filters for producing a plurality of electrical signals representative of the amount of detected infrared light;

means for combining said electrical signals to produce an output signal representative of the concentration of the target gas;

a temperature sensor responsive to the temperature of said infrared detectors; and means, responsive to said temperature sensor, for maintaining the temperature of said infrared detectors at a substantially constant value.

37. The infrared gas analyzer of claim 36 wherein one of said filters is a bandpass filter which has a passband wavelength of approximately 4.3 microns.

38. The infrared gas analyzer of claim 37 wherein another of said filters is a bandpass filter which has a passband wavelength of approximately 4 microns.

39. The infrared gas analyzer of claim 36 wherein said means for producing infrared light includes an infrared light source and a power source producing pulses for energizing said light source.

40. The infrared gas analyzer of claim 36 further comprising a second temperature sensor and a residual temperature trim circuit responsive to said second temperature sensor for modifying said output signal to compensate for large temperature variations of said infrared gas analyzer.

41. The infrared gas analyzer of claim 36 further comprising a humidity sensor and a humidity circuit responsive to said humidity sensor for modifying said output signal to compensate for any residual water sensitivity of said gas analyzer.

42. The infrared gas analyzer of claim 36 wherein one of said filters passes infrared light at a wavelength of approximately 4.5 microns, one of said filters passes infrared light at a wavelength of approximately 4 microns, and one of said filters passes infrared light at a wavelength of approximately 4.3 microns.

43. An infrared gas analyzer for measuring the concentration of nitrous oxide in a sample gas, comprising:

a gas sampling chamber having a first end, a second end, and a striated interior surface;

an infrared light source located at said first end of said gas sampling chamber such that light produced by said infrared light source projects into said gas sampling chamber;

a power source for energizing said infrared light source;

a first bandpass filter, a second bandpass filter, and a third bandpass filter, said bandpass filters located at said second end of said gas sampling chamber;

a first infrared detector responsive to said first bandpass filter for producing a first electrical signal representative of the amount of detected infrared light at a wavelength corresponding to an absorption wavelength of water;

a second infrared detector responsive to said second bandpass filter for producing a second electrical signal representative of the amount of detected infrared light at a wavelength corresponding to an absorption wavelength of carbon dioxide;

a third infrared detector responsive to said third bandpass filter for producing a third electrical signal representative of the amount of detected infrared light at a wavelength corresponding to an absorption wavelength of nitrous oxide;

an electrical circuit for combining said first electrical signal, said second electrical signal, and said third electrical signal to produce an output signal representative of the concentration of the nitrous oxide independently of the carbon dioxide and water in the sample gas;

a temperature sensor responsive to the temperature of said infrared detectors;

a circuit, responsive to said temperature sensor, for maintaining the temperature of said infrared detectors at a substantially constant value; and a control circuit for controlling the intensity of said infrared light source, said control circuit being responsive to one of said infrared detectors for producing a signal input to said power source such that said infrared light source emits infrared light at a substantially constant intensity over time.

44. The infrared gas analyzer of claim 43 wherein said first bandpass filter has a passband wavelength of approximately 4 microns.

45. The infrared gas analyzer of claim 44 wherein said second bandpass filter has a passband wavelength of approximately 4.3 microns.

46. The infrared gas analyzer of claim 45 wherein said third bandpass filter has a passband wavelength of approximately 4.5 microns.

47. The infrared gas analyzer of claim 46 wherein said infrared detectors are pyroelectric detectors.

48. The infrared gas analyzer of claim 43 wherein said gas sampling chamber is constructed of a material selected from the group consisting of aluminum and gold.

49. The infrared gas analyzer of claim 43 further comprising a second temperature sensor and a residual temperature trim circuit responsive to said second temperature sensor for modifying said output signal to compensate for large temperature variations of said infrared gas analyzer.

50. The infrared gas analyzer of claim 49 further comprising a relative humidity sensor and an absolute humidity circuit responsive to said humidity sensor for modifying said output signal to compensate for any residual water sensitivity of said gas analyzer.

51. The infrared gas analyzer of claim 43 wherein said analyzer measures concentrations of nitrous oxide at levels of parts per million.

52. An infrared gas analyzer for measuring low concentrations of a target gas in a sample gas, comprising:

a gas sampling chamber having a first end, a second end, and a striated lining;

an infrared light source located at said first end of said gas sampling chamber such that light produced by said infrared light source projects into said gas sampling chamber;

a power source for energizing said infrared light source;

a plurality of filters located at said second end of said gas sampling chamber, wherein one of said filters is a first bandpass filter for transmitting wavelengths of infrared light at an optimal wavelength for the target gas and at a wavelength associated with a first other gas in the sample gas;

a plurality of infrared detectors each responsive to one of said filters for producing a plurality of electrical signals representative of the amount of detected infrared light; and a circuit for combining said electrical signals to produce an output signal representative of the concentration of the target gas independently of other gases in the sample gas.

53. An infrared gas analyzer for measuring low concentrations of a target gas in a sample gas, comprising:

a gas sampling chamber having a first ends a second end, and a striated interior surface;

an infrared light source located at said first end of said gas sampling chamber such that light produced by said infrared light source projects into said gas sampling chamber;

a power source for energizing said infrared light source;

a plurality of filters located at said second end of said gas sampling chamber, wherein one of said filters is a first bandpass filter for transmitting wavelengths of infrared light at an optimal wavelength for the target gas and at a wavelength associated with a first other gas in the sample gas;

a plurality of infrared detectors each responsive to one of said filters for producing a plurality of electrical signals representative of the amount of detected infrared light; and a circuit for combining said electrical signals to produce an output signal representative of the concentration of the target gas independently of other gases in the sample gas.

* * * * *